(12) United States Patent
Daugherty et al.

(10) Patent No.: US 7,301,164 B2
(45) Date of Patent: Nov. 27, 2007

(54) MEASURING APPARATUS

(75) Inventors: Dennis Charles Daugherty, Grove City, OH (US); Rodney Dale Maxson, Columbus, OH (US); Steven Perry Sturm, Dublin, OH (US)

(73) Assignee: ABB Inc., Columbus, OH (US)

( * ) Notice: Subject to any disclaimer, the term of this patent is extended or adjusted under 35 U.S.C. 154(b) by 469 days.

(21) Appl. No.: 10/768,450

(22) Filed: Jan. 30, 2004

(65) Prior Publication Data

US 2005/0168743 A1    Aug. 4, 2005

(51) Int. Cl.
*G01N 21/86* (2006.01)
*G01N 21/84* (2006.01)

(52) U.S. Cl. .................. 250/559.01; 356/430

(58) Field of Classification Search ............. 250/358.1, 250/339.07, 339.01, 559.16, 226, 559.01, 250/360.1; 356/445, 419, 416, 408
See application file for complete search history.

(56) References Cited

U.S. PATENT DOCUMENTS

| | | | |
|---|---|---|---|
| 4,085,326 A | 4/1978 | Williams | |
| 4,171,918 A | 10/1979 | Mactaggart | |
| 4,278,353 A | 7/1981 | Ostermayer, Jr. | |
| 4,957,770 A | 9/1990 | Howarth | |
| 4,992,657 A | 2/1991 | Reisner | |
| 5,066,865 A | 11/1991 | Wennerberg | |
| 5,233,195 A * | 8/1993 | Hellstrom et al. | 250/360.1 |
| 5,338,361 A | 8/1994 | Anderson et al. | |
| 5,457,539 A | 10/1995 | Sturm | |
| 5,640,244 A | 6/1997 | Hellstrom et al. | |
| 6,246,479 B1 * | 6/2001 | Jung et al. | 356/419 |
| 6,424,416 B1 | 7/2002 | Gross et al. | |
| 6,495,831 B1 | 12/2002 | Hyvarinen et al. | |
| 6,519,037 B2 | 2/2003 | Jung et al. | |
| 6,536,270 B1 | 3/2003 | Henry et al. | |
| 6,643,022 B1 * | 11/2003 | Komppa | 356/445 |
| 6,741,875 B1 * | 5/2004 | Pawluczyk et al. | 600/310 |

(Continued)

FOREIGN PATENT DOCUMENTS

GB    2 077 421 A    12/1981

(Continued)

OTHER PUBLICATIONS

K. Washio, E. Ohue, K. Oda, M. Tanabe, H. Shimamoto, T. Onai, SA 19.6: 95GHz $f_T$ Self-Aligned Selective Epitaxial SiGe HBT with SMI Electrodes, IEEE 1998, p. 19.6-1.

(Continued)

*Primary Examiner*—David Porta
*Assistant Examiner*—Faye Boosalis
(74) *Attorney, Agent, or Firm*—Stevens & Showalter LLP

(57) ABSTRACT

A measuring apparatus is provided having an illumination unit including a source of electromagnetic radiation, fiber optic apparatus and sensing apparatus. The fiber optic apparatus includes first fiber optic structure having an input end for receiving at least a portion of electromagnetic radiation emitted from the radiation source and an output end for directing the received radiation to a web of material, and second fiber optic structure having an input end for receiving radiation reflected from the web of material and an output end for directing the reflected radiation to the sensing apparatus. The sensing apparatus includes a first detector for sensing electromagnetic radiation of a first wavelength band and generating a corresponding first output signal and a second detector for sensing electromagnetic radiation of a second wavelength band and generating a corresponding second output signal indicative of a first property to be measured of the web of material.

20 Claims, 4 Drawing Sheets

U.S. PATENT DOCUMENTS

| | | | |
|---|---|---|---|
| 6,960,769 B2 * | 11/2005 | Burk et al. ............ | 250/339.07 |
| 6,961,126 B2 * | 11/2005 | Belotserkovsky et al. .. | 356/419 |
| 2002/0110487 A1 | 8/2002 | Samsoondar | |
| 2002/0192116 A1 | 12/2002 | Vuong | |
| 2004/0065829 A1 * | 4/2004 | Burk et al. ............ | 250/339.07 |

FOREIGN PATENT DOCUMENTS

| JP | 62201327 | 9/1987 |
|---|---|---|
| JP | 2003116782 | 4/2003 |
| WO | WO 95/19562 A1 | 7/1995 |
| WO | WO 01/16578 A1 | 3/2001 |

OTHER PUBLICATIONS

Egor Alekseev, Kyushik Hong, Dimitris Pavlidis, Don Sawdai, Apostolos Samelis, InGaAs/InP PIN Diodes for Microwave and Millimeter-Wave Switching and Limiting Applications, International Semiconductor Device Research Symposium 1996, Solid State Electronics Laboratory, Department of Electrical Engineering and Computer Science, Univ. of MI, Ann Arbor, MI.

* cited by examiner

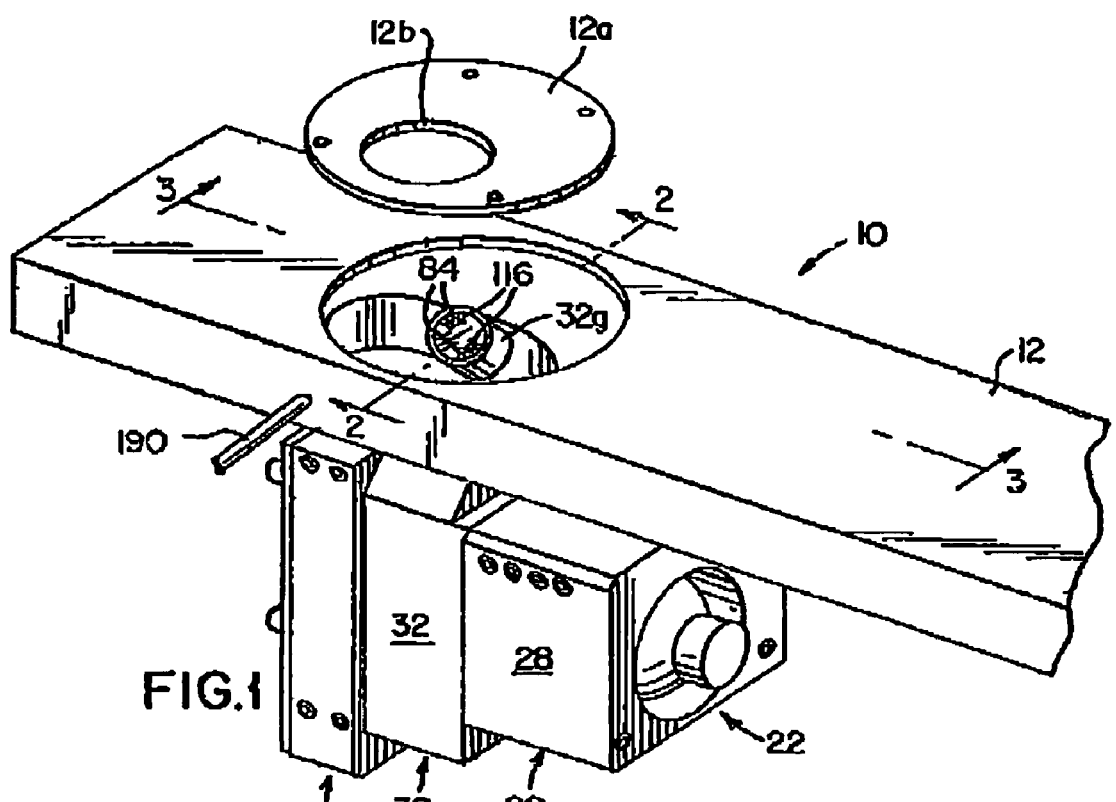
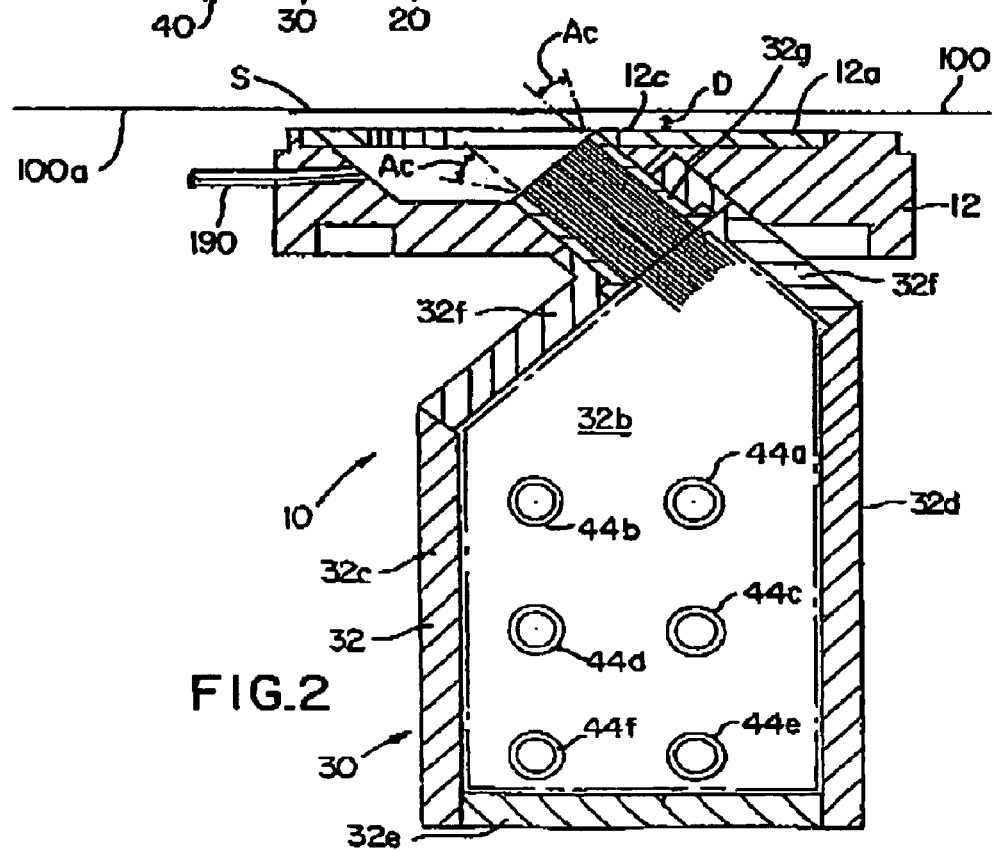

MEASURING APPARATUS

BACKGROUND OF THE INVENTION

The present invention relates in general to instruments for measuring material properties and, more particularly, to an improved instrument for on-line measurement of material properties by scatter-mode multi-wavelength differential absorption spectroscopy.

U.S. Pat. No. 5,338,361 discloses a sensor for on-line coating measurements of a moving paper sheet. The sensor includes a light source for transmitting a beam of infrared radiation toward the moving sheet. The infrared radiation encompasses a broad range of wavelengths. Different coatings, such as clay and latex, as well as moisture absorb different wavelengths in varying amounts. In one embodiment, a receiver is located on the same side of the moving sheet as the source for measuring the intensity of the reflected portion of the beam radiation. The receiver comprises at least one beam splitter and a plurality of separate detectors. A band pass filter is associated with each detector to pass that portion of the spectrum falling within the pass band. Hence, a first band pass filter, associated with a first detector, passes wavelengths of the spectrum which are strongly absorbed by a first coating material, e.g., latex. A second band pass filter, associated with a second detector, passes wavelengths of the spectrum which are strongly absorbed by a second coating material, e.g., clay. A third band pass filter, associated with a third detector, passes wavelengths of the spectrum where the radiation is strongly absorbed by the base sheet, but is only weakly absorbed by the first and second coating components. A fourth band pass filter, associated with a fourth detector, passes wavelengths of the spectrum where the radiation is strongly absorbed by moisture.

A first disadvantage of the sensor disclosed in the '361 patent relates to the long paths from the radiation source to the paper sheet and from the paper sheet to the detectors. These long paths result in a decrease in the total amount of signal received by the detectors. A second disadvantage is that the path lengths to the various detectors are not the same, thereby resulting in the detectors having different fields of view. It is also noted that the reflected radiation should be aligned exactly along the axis of the beam splitter, which is problematic to accomplish.

A similar reflective infrared measuring apparatus is also known comprising a substantially clear window through which a light beam exits before impinging upon a moving substrate. Any dust on the window results in light being back scattered toward one or more radiation detectors. To prevent the scattered light from reaching the radiation detectors, a blocking member is provided in the sensor housing. While the blocking member functions to shield a significant portion of light scattered by dust, the blocking member also shields a portion of the light reflected from the moving substrate from reaching the detectors, which reduces the total sensed radiation scattered back by the substrate reducing the instrument signal-to-noise ratio. Further, because the light emitted by the source passes through a different area of the window as compared to the light scattered back by the substrate, the dust on the window, which is typically non-uniform in distribution, may influence the properties of the light impinging on the substrate differently than the properties of the light back scattered by the substrate. This sensor also suffers from the same first and second disadvantages noted above with regard to the sensor disclosed in the '361 patent.

There is a need for an improved infrared measuring apparatus wherein the path lengths to the detectors are substantially equal in length such that the detectors have substantially the same fields of view and the distances between the light source and the moving substrate and the moving substrate and the detectors are minimized.

SUMMARY OF THE INVENTION

In accordance with the present invention, an improved instrument is provided for on-line sensing of material properties by scatter-mode multi-wavelength differential absorption spectroscopy.

In accordance with a first aspect of the present invention, a measuring apparatus is provided comprising: an illumination unit including a source of electromagnetic radiation; fiber optic apparatus and sensing apparatus. The fiber optic apparatus includes first fiber optic structure having an input end for receiving at least a portion of electromagnetic radiation emitted from the radiation source and an output end for directing the received radiation to a web of material, and second fiber optic structure having an input end for receiving radiation reflected from the web of material and an output end for directing the reflected radiation to a sensing apparatus. The sensing apparatus comprises a first detector for sensing electromagnetic radiation of a first wavelength band and generating a corresponding first output signal and a second detector for sensing electromagnetic radiation of a second wavelength band and generating a corresponding second output signal indicative of a first property to be measured of the web of material.

The first fiber optic structure preferably comprises a bundle of first optical fibers having first input ends for receiving the portion of electromagnetic radiation emitted from the radiation source and first output ends for directing the received radiation onto the web of material. The second fiber optic structure preferably comprises a bundle of second optical fibers having second input ends for receiving radiation reflected from the web of material and second output ends for directing the reflected radiation to the sensing apparatus. The first output ends may be randomly intermixed with the second input ends.

The electromagnetic radiation of a first wavelength band may comprise electromagnetic radiation of a first infrared wavelength band and the electromagnetic radiation of a second wavelength band may comprise electromagnetic radiation of a second infrared wavelength band. The first output signal may comprise a reference signal and the second output signal may be compared to the first output signal via a processor to determine the first property of the web of material. It is contemplated that the first and second wavelength bands may comprise ultra-violet, visible, near-infrared or mid-infrared wavelength bands.

The sensing apparatus may further comprise: third, fourth, fifth and sixth detectors. The third detector senses electromagnetic radiation of a third infrared wavelength band and generates a corresponding third output signal indicative of a second property to be measured of the web of material. The third output signal is compared to the first output signal via a processor to determine the second property of the web of material. The fourth detector senses electromagnetic radiation of a fourth infrared wavelength band and generates a corresponding fourth output signal indicative of a third property to be measured of the web of material. The fourth output signal is compared to the first output signal via a processor to determine the third property of the web of material. The fifth detector senses electromagnetic radiation of a fifth infrared wavelength band and generates a corresponding fifth output signal indicative of a fourth property to be measured of the web of material. The fifth output signal is compared to the first output signal via a processor to determine the fourth property of the web of material. The sixth detector senses electromagnetic radiation of a sixth infrared wavelength band and generates a corresponding sixth output signal indicative of a fifth property to be measured of the web of material. The sixth output signal is compared to the first output signal via a processor to determine the fifth property of the web of material.

The first output ends and the second input ends may be positioned at an angle of from about 30 degrees to about 60 degrees to the web of material such that the second input ends receive substantially only diffuse electromagnetic radiation reflected from the web of material.

The first optical fibers may be randomly routed such that the first input and output ends are randomly positioned and the second optical fibers may be randomly routed such that the second input and output ends are randomly positioned.

All of the second optical fibers are preferably of substantially the same length.

The illumination unit may further comprise a support to which the electromagnetic radiation source is coupled. The measuring apparatus preferably further comprises a chopper mechanism including a chopper element. The illumination unit support comprises a first slot through which the chopper element is permitted to enter so as to prevent light generated by the electromagnetic radiation source from passing through a main illumination opening in the illumination unit support to the input end of the first fiber optic structure. The measuring apparatus may also further comprise a standardize mechanism including a shutter. The illumination unit support comprises a second slot through which the shutter is permitted to pass so as to prevent electromagnetic radiation generated by the electromagnetic radiation source from passing through an opening to an input end of a third fiber optic structure.

The third fiber optic structure may comprise a bundle of third optical fibers having third input ends for receiving at least a portion of the electromagnetic radiation emitted from the electromagnetic radiation source when the shutter is absent from the second slot and third output ends for directing the light to the sensing apparatus.

The fiber optic apparatus may further comprise an optical fiber housing in which at least portions of the first and second fiber optic structures are housed.

In accordance with a second aspect of the present invention, a measuring apparatus is provided comprising: an illumination unit comprising an electromagnetic radiation source; electromagnetic radiation guide apparatus; sensing apparatus; and a processor. The electromagnetic radiation guide apparatus may include a first radiation guide structure having an input end for receiving at least a portion of radiation emitted from the electromagnetic radiation source and an output end for directing the received radiation onto a web of material, and a second radiation guide structure having an input end for receiving radiation reflected from the web of material and an output end for directing the reflected radiation to a sensing apparatus. The sensing apparatus may comprise a first detector for sensing electromagnetic radiation of a first wavelength band and generating a corresponding first output signal and a second detector for sensing electromagnetic radiation of a second wavelength band and generating a corresponding second output signal. The processor receives the first and second output signals and determines a property of the web of material using the first and second output signals.

The first radiation guide structure may comprise a bundle of first optical fibers having first input ends for receiving the portion of the electromagnetic radiation emitted from the electromagnetic radiation source and first output ends for directing the received radiation onto the web of material. The second radiation guide structure may comprise a bundle of second optical fibers having second input ends for receiving electromagnetic radiation reflected from the web of material and second output ends for directing the reflected radiation to the sensing apparatus. The first output ends are preferably randomly intermixed with the second input ends.

The sensing apparatus may further comprise: a third detector for sensing electromagnetic radiation of a third wavelength band and generating a corresponding third output signal; a fourth detector for sensing electromagnetic radiation of a fourth wavelength band and generating a corresponding fourth output signal; a fifth detector for sensing electromagnetic radiation of a fifth wavelength band and generating a corresponding fifth output signal; and a sixth detector for sensing electromagnetic radiation of a sixth wavelength band and generating a corresponding sixth output signal.

In accordance with a third aspect of the present invention, an optical system is provided for directing electromagnetic radiation toward a web of material and for receiving radiation backscattered from the web. The system comprises: a bundle of first optical fibers having first input ends for receiving electromagnetic radiation and directing the electromagnetic radiation to a web of material from first output ends; and a bundle of second optical fibers having second input ends for receiving electromagnetic radiation backscattered from the web of material and second output ends for passing backscattered radiation received from the web to at least one electromagnetic radiation output port, i.e., a detector ferrule. The first output ends are preferably randomly intermixed with the second input ends.

BRIEF DESCRIPTION OF THE DRAWINGS

FIG. 1 is a perspective view of an infrared measuring apparatus constructed in accordance with the present invention;

FIG. 2 is a cross sectional view of the apparatus illustrated in FIG. 1 taken along section line 2-2 through fiber optic apparatus;

DETAILED DESCRIPTION OF THE INVENTION

Figure 3:
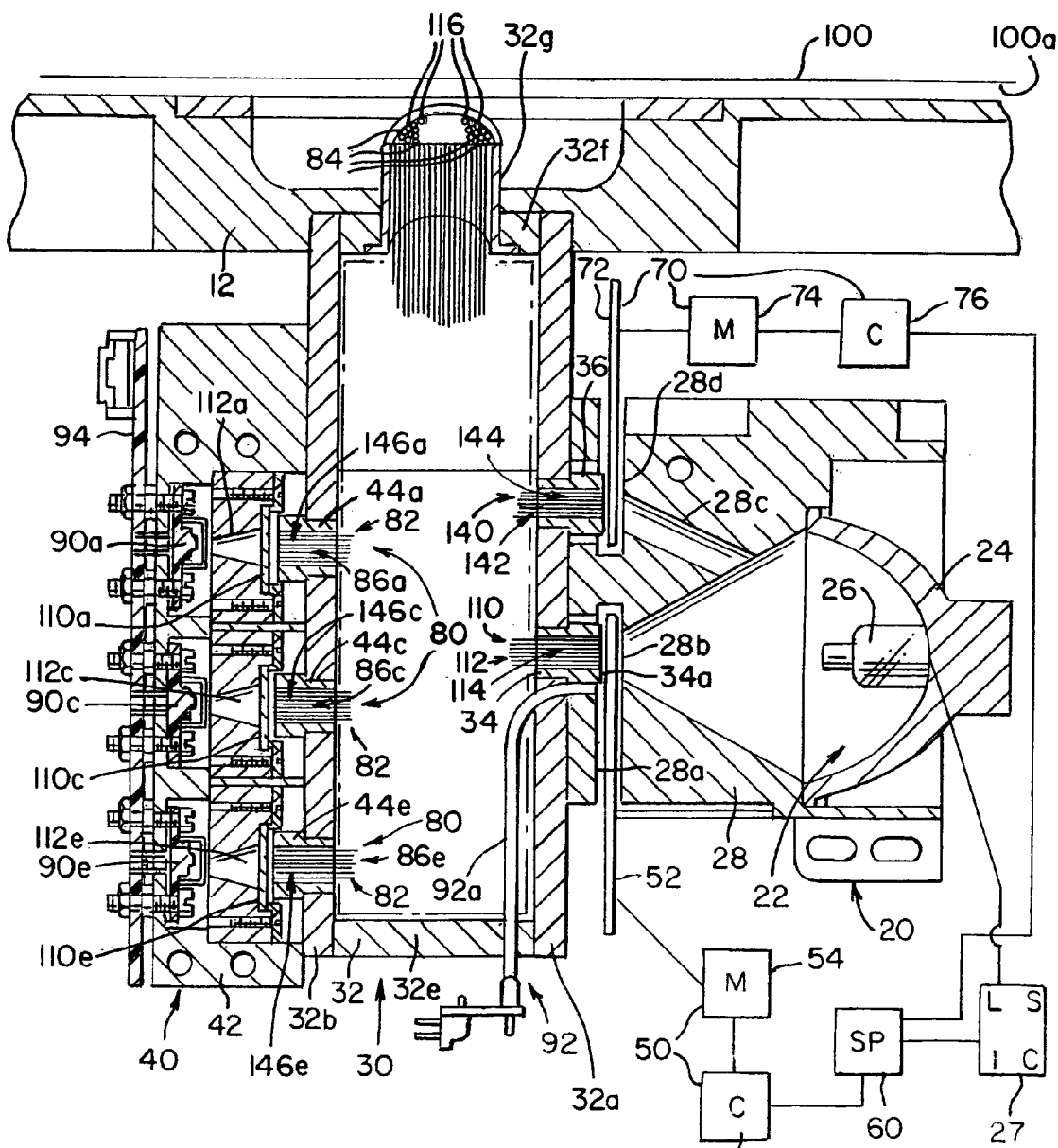
FIG. 3 is a view taken along view line 3-3 in FIG. 1.

Referring now to the drawings, in which like-referenced characters indicate corresponding elements throughout the several views, attention is first drawn to FIGS. 1-3, which show an embodiment of a measuring apparatus 10 in accordance with the present invention for measuring characteristics of a web product. While the present invention is generally applicable to measurement of a variety of web products being manufactured, the present invention will be described herein with reference to a paper web 100 (not shown in FIG. 1). Measuring apparatus 10 includes an illumination unit 20, fiber optic apparatus 30 and sensing apparatus 40. The measuring apparatus 10 further comprises a base plate 12 to which the illumination unit 20, the fiber optic apparatus 30 and the sensing apparatus 40 are coupled. A faceplate 12a including an opening 12b is coupled to the base plate 12. The base plate 12 in combination with the illumination unit 20, the fiber optic apparatus 30 and the sensing apparatus 40 move in a cross scan direction, which is transverse to the direction in which the web 100 moves in a process direction.

The illumination unit 20 utilizes a broad bandwidth or white light source 22 (hereinafter referred to as the light source; also referred to herein as a source of electromagnetic radiation) that has a light intensity that is controlled by the level of the voltage applied to the light source. The light source 22 comprises a focused projection lamp comprising, for example, a gold plated reflector 24 and a lamp 26 with a tungsten filament surrounded by halogen gas, see FIG. 3. The reflector 24 is coupled to an illumination unit support 28, which, in turn, is coupled to a fiber optic apparatus housing 32. Since the sensing apparatus 40, in the illustrated embodiment, detects radiation in the near infrared range (1-3 μm), the voltage provided to the light source 22 may be reduced below a design voltage to shift its emission curve away from the visible spectrum, from a design "color temperature" of about 3500K to a target of about 2600K so as to extend the life of the light source 22. Thus, the light source 22 preferably emits infrared (and visible) wavelengths, which light is focused to a spot of about one centimeter diameter at a controlled focal distance located adjacent an edge 34a of a fiber optic source ferrule 34 forming part of the fiber optic apparatus housing 32. The light source 22 may be air-cooled using conventional cooling structure (not shown) or otherwise cooled to increase lamp life and to reduce heat effects on the measuring system.

It is also contemplated that the sensing apparatus 40 may detect electromagnetic radiation in the ultra-violet, visible or mid-infrared range, and wherein the light source 22 emits radiation in a corresponding range.

Coupled to the illumination unit 20 is a chopper mechanism 50 comprising a chopper 52 (also referred to herein as a "chopper element"), a chopper stepper motor 54 and a controller 56. The chopper motor 54 functions to cause the chopper 52 to interrupt light emitted by the light source 22 for a few milliseconds or a longer period, as discussed further below. The chopper 52 travels in a first slot 28a defined in the illumination unit support 28. The chopper 52, when interrupting the light generated by the source 22, substantially fully prevents light from passing through a main illumination opening 28b in the illumination unit support 28 to the fiber optic source ferrule 34. The chopper 52 may be constructed in essentially the same manner as the shutter flag disclosed in copending U.S. patent application Ser. No. 10/264,080, entitled "An Infrared Measuring Apparatus and Method for On-line Application in Manufacturing Processes," the disclosure of which is incorporated herein by reference.

The chopper motor 54 may comprise a stepper motor or other appropriate drive device that moves the chopper 52 so that the chopper 52 selectively interrupts the light source 22. The controller 56 comprises an electrically programmable logic device (EPLD) and a conventional motor driver, one of which is commercially available from ST Microelectronics under the product designation "L6506D IC." The controller 56 functions to control the motor 54 based on instructions received from the system processor 60, such as 1) to effect reciprocating movement of the chopper 52 during normal material property measurement operation of the apparatus 10 so as to allow "dark condition" values, discussed below, to be determined; 2) to move the chopper 52 to a light or radiation blocking position during a standardize operation, discussed below, so as to allow "dark-signal" and "light-signal" values to be determined; and 3) to stop movement of the chopper 52 to allow diagnostic operations to be performed.

Further coupled to the illumination unit 20 is a standardize shutter mechanism 70 comprising a standardize shutter 72, a shutter solenoid 74 and a controller 76. The standardize shutter solenoid 74 functions to cause the standardize shutter 72 to move into and out of the path of light generated by the light source 22 and passing through an opening or bore 28c formed in the illumination unit support 28. When positioned so as to block the light emitted through the bore 28c, the standardize shutter 72 is positioned in a second slot 28d defined in the illumination unit support 28 so as to substantially fully prevent light from passing into a standardize ferrule 36 forming part of the fiber optic apparatus housing 32.

In place of the standardize shutter solenoid 74, any other appropriate drive device may be provided that moves the standardize shutter 72 so that the shutter 72 selectively interrupts the light passing through the bore 28c. The controller 76 comprises an electrically programmable logic device (EPLD) and a conventional solenoid driver, one of which is commercially available from International Rectifier under the product designation IRFR2405. The controller 76 functions to control the solenoid 74 based on instructions received from the system processor 60, such as to effect movement of the shutter 72 during a standardization operation, discussed below.

The fiber optic apparatus housing 32, which forms part of the fiber optic apparatus 30, comprises first and second sidewalls 32a and 32b, respectively, see FIG. 3. The first side wall 32a is coupled to the illumination unit 20 and the second side wall 32b is coupled to a sensing apparatus housing 42. The fiber optic ferrule 34 and the standardize ferrule 36 are mounted in the first side wall 32a. The fiber optic source ferrule 34 has a diameter of approximately 0.24 inch and the standardize ferrule 36 has a diameter of approximately 0.181 inch. In the illustrated embodiment first, second, third, fourth, fifth and sixth detector ferrules 44a-44f are mounted in the second sidewall 32b, see FIGS. 2 and 3. Each of the ferrules 44a-44f has a diameter of approximately 0.245 inch. The fiber optic apparatus housing 32 also comprises front and rear walls 32c and 32d, respectively, a base wall 32e and upper walls 32f. A generally cylindrical fiber holding member 32g extends from one of the upper walls 32f at an angle of from about 30 degrees to about 60 degrees and preferably about 45 degrees relative to the web, see FIG. 2. The generally cylindrical member 32g has a diameter of approximately 0.625 inch.

Figure 5:
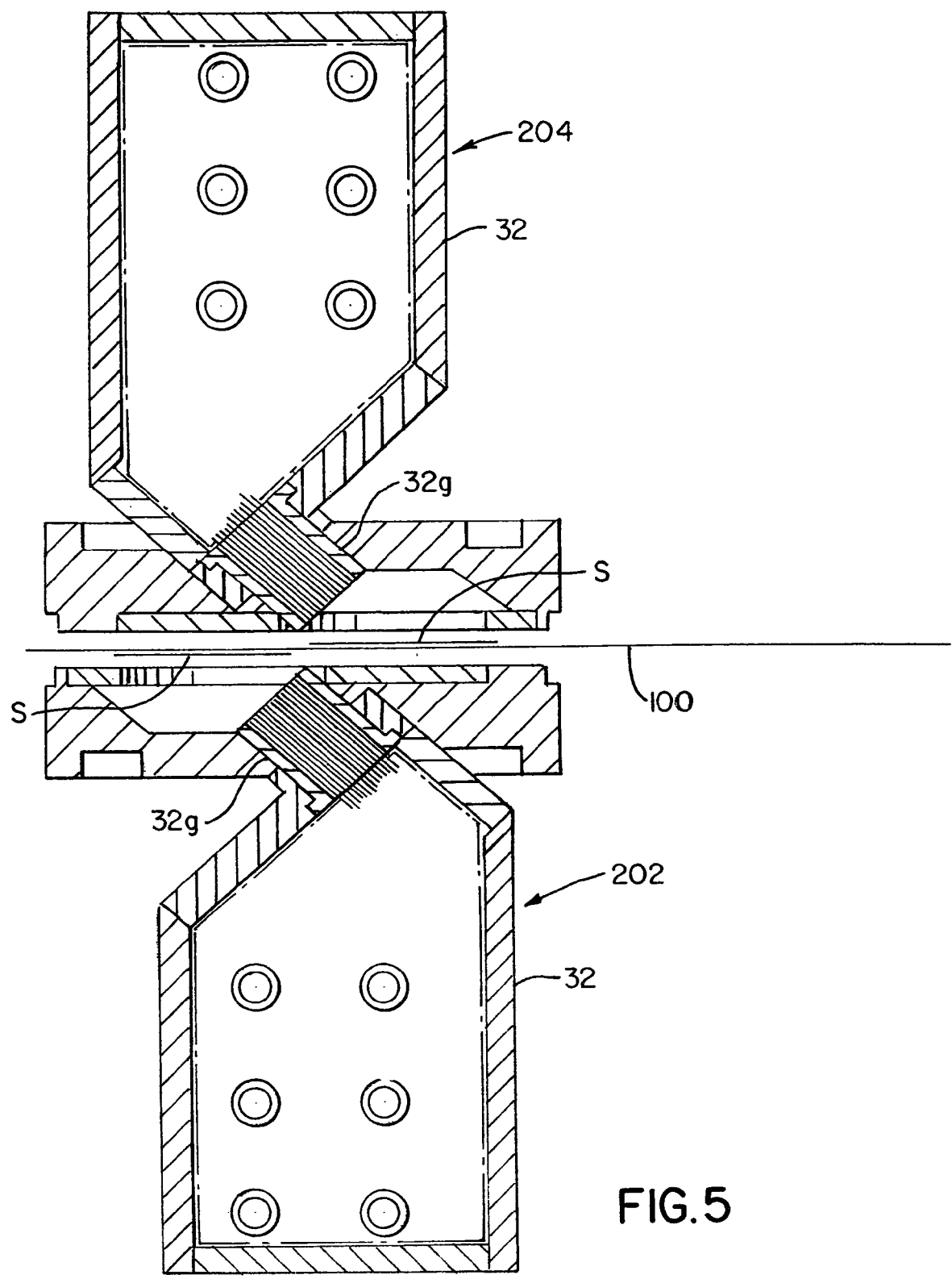
FIG. 5 is a cross sectional view of a system comprising two infrared measuring apparatuses of the present invention.

The fiber optic apparatus 30 further comprises first fiber optic structure 110 comprising a bundle of first optical fibers 112 having first input ends 114 positioned in the fiber optic source ferrule 34 for receiving a portion of light emitted from the light source 22 and first output ends 116 positioned in the cylindrical member 32g for directing the received light onto the web 100, thereby generating a spot S of light on the web 100, see FIGS. 2, 3 and 5. The fiber optic apparatus 30 additionally comprises second fiber optic structure 80 comprising a bundle of second optical fibers 82 having second input ends 84 positioned in the cylindrical member 32g for receiving light diffusively reflected from the web of material 100 and second output ends 86 for directing the reflected light to the sensing apparatus 40. The second output ends are separated into sub-bundles 86a-86f, equal in number to the detector ferrules 44a-44f provided. Each of the sub-bundles 86a-86f may comprise approximately the same number of output ends 86. In a working embodiment, approximately 6800 first optical fibers 112, each having a diameter of about 0.003 inch are provided, and approximately 40900 second optical fibers 82 (i.e., 6820 fibers×6 sub-bundles 86a-86f), each having a diameter of about 0.003 inch are provided. The first optical fibers 112 are all of substantially the same length and the second optical fibers 82 are all of substantially the same length to reduce variations in the light paths from the light source 22 to detector elements, which elements will be discussed below. The fibers 112 and 82 are preferably formed from an infrared transmitting fiber optic material, such as fiber optic material manufactured by Schott Glass of Germany and sold by Schott-Fostec in Auburn, N.Y. under the product designation "IR1."

Preferably, the first output ends 116 are randomly intermixed with the second input ends 84 so as to allow the second input ends 84 to sense or "see" substantially the same illuminated spot S on the web 100 as the first output ends 116 even as the passline distance D, see FIG. 2, between the web 100 and cylindrical member 32g varies. In the illustrated embodiment, the nominal passline distance D is 3.5 mm, as measured between the web 100 and the upper surface 12c of the faceplate 12a, see FIG. 2. While not illustrated in FIG. 2, it is contemplated that the uppermost edge of the cylindrical member 32g nearest the web 100 may be recessed below and spaced from the upper surface 12c of the faceplate 12a by about 1 mm to about 1.5 mm. Also, it is preferred that substantially no specularly reflected light from the web 100 be received by the second input ends 84. Specularly reflected light reflects directly from a first surface 100a of the web 100 so as to prevent it from interacting with the absorption centers in the web 100. Hence, such light provides little information regarding web properties.

Light is emitted by the first output ends 116 of the first fibers 112 as a cone of light having an angle $A_C$ of approximately 30 degrees, see FIG. 2. So as to prevent specularly reflected light from being received by the second input ends 84, the first output ends 116 are positioned at an angle of from about 30 degrees to about 60 degrees and preferably about 45 degrees relative to the web 100, see FIG. 2. The first and second optical fibers 112 and 82 are tightly bundled in the cylindrical member 32g such that the angle of the cylindrical member 32g defines the angle at which the first and second fibers 112 and 82 are positioned relative to the web 100.

It is noted that the exposed outer edges of the first output ends 116 and the second input ends 84 are polished. Also, a pressurized air supply source (not shown) supplies air to an air supply tube 190 to blow off dust which might accumulate on the polished outer surface of the first output ends 116 and the second input ends 84, see FIG. 2.

The routing of the first optical fibers 112 may occur so that the first input ends 114 are intentionally randomly positioned in the fiber optic ferrule 34 and the first output ends 116 are intentionally randomly positioned in the cylindrical member 32g such that if an image were projected onto the first input ends 114, that image would have no relationship with the light pattern viewed at the first output ends 116. Likewise, it is preferred that the routing of the second optical fibers 82 occur so that the second input ends 84 are intentionally randomly positioned in the cylindrical member 32g and the second output ends 86 are intentionally randomly positioned in the ferrules 44a-44f such that if an image were projected onto the second input ends 84, that image would have no relationship with the light pattern viewed at the second output ends 86.

Figure 4:
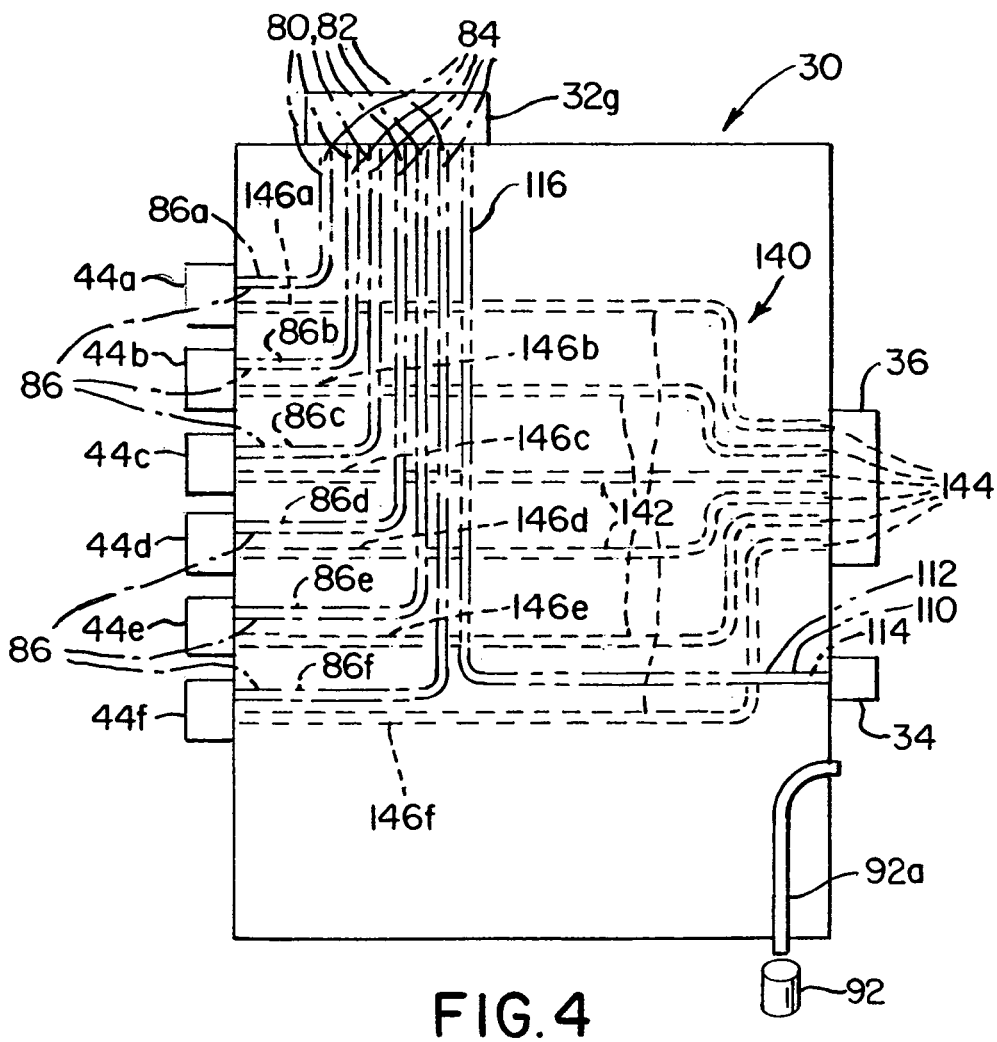
FIG. 4 is a schematic view of the fiber optic apparatus of the infrared measuring apparatus of FIG. 1.

The fiber optic apparatus 30 still further comprises third fiber optic structure 140 comprising a bundle of third optical fibers 142 having third input ends 144 positioned in the standardize ferrule 36 for receiving light passing through the bore 28c and third output ends for directing the light to the sensing apparatus 40, see FIGS. 2, 3 and 4. The third output ends are separated into sub-bundles 146a-146f, schematically illustrated in FIG. 4, equal in number to the detector ferrules 44a-44f provided. In each of the detector ferrules 44a-44f, the third output ends 146 are randomly intermixed with the second output ends 86. Each of the sub-bundles 146a-146f may comprise approximately the same number of output ends 146, e.g., approximately 670 third fiber output ends. In a working embodiment, approximately 4000 third optical fibers 142 (i.e., 670 fibers×6 sub-bundles 146a-146f), each having a diameter of about 0.003 inch, are provided. The third optical fibers 142 are all of substantially the same length. The fibers 142 are preferably formed from an infrared transmitting fiber optic material, such as fiber optic material manufactured by Schott Glass of Germany and sold by Schott-Fostec in Auburn, N.Y. under the product designation "IR1."

The sensing apparatus housing 42 contains detector elements 90a-90f (detectors elements 90a, 90c and 90e are illustrated in FIG. 3; detector elements 90b, 90d, 90f, which correspond respectively to ferrules 44b, 44d and 44f, are also provided and are located directly in front of the detector elements 90a, 90c and 90e shown in FIG. 3), which preferably define absorption wavelength detector elements. The detector elements 90a-90f are also referred to herein as "detectors." The detector elements 90a-90f may be InGaAs detectors but may comprise other detector technologies depending on desired properties. For example, Lead Selenide or Platinum Silicide detectors may be used if longer wavelengths are desired to be measured. In the illustrated embodiment, the detector elements 90a-90f comprise InGaAs detectors, which are commercially available from Hamamatu under the product designations G8372-06; G8792-01 and G 7953-21. The use of separate wavelength detector elements, such as the detector elements 90a-90f, enables the measuring apparatus 10 of the present invention to measure the energy at corresponding wavelengths diffusively reflected from the same sample portion of the web 100 substantially simultaneously allowing for simultaneous detection of a plurality of properties/characteristics of the web 100.

Figure 3A:
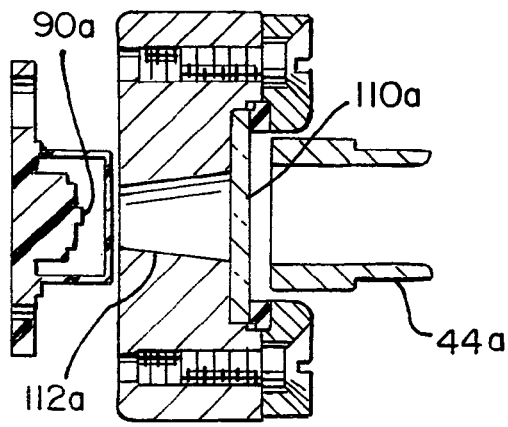
FIG. 3A is a cross sectional view of a single detector element and its corresponding bandpass filter.

Referring again to FIG. 3, light signals from the sub-bundles 86a-86f (only sub-bundles 86a, 86c, 86e of sub-bundles 86a-86f are shown in FIG. 3) travel through bandpass filters 110a-110f (only filters 110a, 110c, 110e are illustrated in FIG. 3; filters 110b, 110d and 110f correspond to detector elements 90b, 90d and 90f and are located directly in front of the filters 110a, 110c, and 110e shown in FIG. 3) and light collectors 112a-112f (only collectors 112a, 112c, 112e are illustrated in FIG. 3; collectors 112b, 112d and 112f correspond to detector elements 90b, 90d and 90f and are located directly in front of the collectors 112a, 112c and 112e shown in FIG. 3), preferably conical in shape. Detector element 90a, bandpass filter 110a and light collector 112a are also illustrated in FIG. 3A. Alternatively, lenses can be used in place of the light collectors 112a-112f. Each bandpass filter is selected so as to pass infrared radiation falling within a predefined band of the infrared spectrum which is readily absorbed by the property/characteristic, e.g., cellulose fibers, moisture, latex binder, clay, calcium carbonate, or plastic films, its corresponding detector element is measuring.

As noted above, light diffusively reflected from the web 100 is received by the second optical fibers 82. Due to the second output ends of the second optical fibers being separated into sub-bundles 86a-86f, the light collected by the second fibers 82 is separated into corresponding light portions such that those light portions are received by the detector elements 90a-90f after first being filtered by a corresponding bandpass filter 110a-110f. Hence, the second fibers 82 function as light beam distributors.

The detector elements 90a-90f are mounted to a detector board 94 that includes circuitry (not shown) for processing signals generated by the detector elements 90a-90f. In the illustrated embodiment, the signals from each of the wavelength detector elements 90a-90f comprise current signals corresponding to the amount of reflected infrared radiation falling within a corresponding specific wavelength band. Those current signals are processed by current-to-voltage pre-amplifiers, provided on the detector board 94, each of which corresponds to one of the detector elements 90a-90f, also located on the detector board 94. Output voltage signals from the pre-amplifiers are provided to a gain board, which processes those signals in a manner to be described below. From the gain board, analog signals are provided to the system processor 60.

A silicon "synch" detector 92, comprising a standard silicon photocell capable of sensing visible light, is positioned adjacent to the housing 32. Such a detector 92 is commercially available from Fairchild Semiconductor under the product designation QSC114. Further provided is a synch light pipe 92a extending to a position adjacent to the main illumination opening 28b. The detector 92 used in the illustrated embodiment is sensitive to the visible light spectrum as well as the infrared spectrum out to 1.1 microns. The silicon "synch" detector 92 generates signals indicating when the chopper 52 has been moved to a position so as to interrupt light from the light source 22. It is believed that the visible light detector 92 provides a much better signal-to-noise ratio regarding the chopper position as compared to an infrared detector element such as one of the elements 90a-90f.

In operation, infrared light from the light source 22 is transmitted by the first optical fibers 112 as a spot S of light onto a small area, hereinafter the "measured area" or single sample section, of the moving paper web 100 located adjacent to the cylindrical member 32g. The material of the paper web 100 and any coatings thereon interact with this incident infrared light and absorb or reflect the various spectral components in accordance with the properties/characteristics being measured, e.g., cellulose fibers, moisture or coatings provided on the paper sheet, such as clay, latex binder, calcium carbonate or plastic, all of which may absorb specific wavelengths of the incident infrared light differently. The characteristics being measured may include any properties with specific and discrete infrared absorption bands, such as moisture, cellulose fibers, clay, latex binder, calcium carbonate, plastic, etc. As noted above, the diffusively reflected light is received by the second input ends 84 of the second optical fibers 82 and is distributed by the second output end sub-bundles 86a-86f to the bandpass filters 110a-110f and then to the detector elements 90a-90d.

Because the routing of the first and second optical fibers 112 and 82 occurs in a random manner, any non-uniformity of the reflection of light from the web 100 will have approximately the same influence at all light collectors 112a-112f, bandpass filters 110a-110f and detectors 90a-90f.

As noted above, the detector elements 90a-90f preferably comprise InGaAs detector elements. More specifically, the detector elements 90a-90f comprise multiple extended bandgap Indium Gallium Arsenide (InGaAs) detector elements 90a-90f. Although any size detector elements may be used in the present invention, InGaAs detector elements having a diameter of approximately one millimeter are currently preferred. The "wavelength" detector elements 90a-90f measure infrared light over different wavelength bandpasses substantially simultaneously and output corresponding signals. Each specific bandpass is selected to indicate the spectra absorption property/characteristic of interest of the web 100. For this reason each detector element 90a-90f may have a slightly different design, which is called extended bandgap, to optimize their ability to detect infrared in a specific waveband of interest. A single type of InGaAs PIN diode typically does not provide good photo-sensitivity over all the different wavelengths. The detectors 90a-90f are of three different types that have different proportions of Indium to Gallium, such as those commercially available from Hamamatu under the product designations G8372-06; G8792-01 and G 7953-21. This gives the detectors different band gaps, which makes the individual detectors more sensitive to the desired wavelengths.

The bandpass filters 110a-110f may comprise tuned dichroic interference filters. These tuned dichroic interference filters can be tilted to shift the center wavelength of the pass bands to longer wavelengths for light that is not normal to the filter or the angles of light passing through them can be controlled by adjusting the reflectivity of the light collectors 112a-112f or by aperturing the fiber optics.

As is well known in infrared spectroscopic measurement, a first wavelength or desired spectral absorption wavelength is selected where absorption by the web property/characteristic, e.g., moisture, cellulose fibers, latex binder, clay, calcium carbonate, etc., to be measured is high. Then a second nearby wavelength or reference wavelength is selected where absorption by the web property/characteristic to be measured is low. A function of the ratio of the infrared light at these two wavelengths reflected from the web 100 is correlated to the area weight or amount of the property/characteristic on or in the web 100 to be measured. For water, an area weight moisture measurement is converted to percent moisture by dividing the area weight moisture measurement by the total weight of the web in that same area. This total web weight can be inferred from a function of the measured paper fiber weight.

Conventional InGaAs detector elements are sensitive to infrared light no longer than about 1.7 μm in wavelength and have relatively short time constants, in the ten nanoseconds range. Some web properties/characteristics desired to be measured require detection of longer wavelengths. Several commercial manufacturers, such as PerkinElmer, ElectroOptics and Hamamatsu USA, offer extended InGaAs detector elements, in which the wavelength sensitivity extends to as long as 2.7 μm. A characteristic of this extension of the detected wavelength range is that certain performance parameters degrade, specifically a property commonly called the "shunt resistance." As a result of low shunt resistance, even a small offset voltage (micro Volts) on the detector element will generate dark currents comparable to the measured signal. This results in higher noise on the signal and will limit maximum gain unless compensated.

The shunt resistance is highly temperature dependent. By cooling detectors, the dark current can be decreased.

Thermoelectric cooling of the active elements of the detector elements 90a-90f may cause the detector elements 90a-90f to operate at similar shunt resistances. Therefore, as the extension of the sensitive wavelength increases, those detector elements 90a-90f operating at extended wavelengths should operate at a cooler temperature. This equalizing of the operational "shunt resistance" of the detector elements 90a-90f permits minimizing the noise floor of the overall measurement that may be made by mathematical functional combination of all detector signals, providing the optimum measurement performance. Thermoelectric cooling devices, such as Peltier coolers, and temperature measuring devices, such as thermistors, are currently available as a built-in part of commercially available InGaAs detector elements. Additionally, InGaAs detector elements may use compressed air heatsinking, if needed, to achieve desired cooling temperatures. Preferably, these cooling devices maintain the cooled detector elements within three degrees Celsius of their setpoint. Preferably, a portion of the InGaAs detector elements 90a-90f, such as elements operating at extended wavelengths, e.g., those detecting wavelengths equal to or greater than 2.1 microns, are temperature controlled while other InGaAs detector elements, such as elements operating at a non-extended wavelength, e.g., less than 2.1 microns, are not temperature controlled. The ability to accurately compensate for the reduced temperature sensitivity of the extended InGaAs detector elements enables multiple InGaAs detector elements 90a-90f to obtain signals substantially simultaneously, in contrast to previous measuring devices.

InGaAs photodiode detectors are typically operated with a reverse bias of 3 to 5 VDC. Increasing the reverse bias (up to the breakdown limit) improves detector response time. High reverse bias means charges (electrons and holes) are collected sooner and junction capacitance is lower. However, when a reverse bias is applied, some current will flow without illumination, this current is called "dark current" and is a function of the shunt resistance, as discussed above. A change in the temperature of a photodiode changes dark current (shunt resistance). In the present invention, it is preferred to operate the detectors near zero bias. This is to minimize the requirement for rigorous temperature control of each detector. Operation at near zero bias lowers the detector cut-off frequency; however, the resulting cut-off frequency is still approximately 1 Megahertz. This somewhat slower response exceeds the requirements for the current application wherein detector signals are sampled at 5 Kilohertz. In the present invention, variations in detector temperature up to 5 degrees Celsius are allowed without frequent "dark condition" correction (described below) and without deleterious influence on measured material properties.

The operation of the chopper mechanism 50 will now be described. During normal material property measurement operation of the apparatus 10, the chopper 52 periodically blocks light, emitted by the light source 22, from passing through opening 28b, thereby allowing the residual signal at each detector element 90a-90f to be measured in the absence of source illumination. The residual signal is the signal component not resulting from the measured parameter, i.e., not resulting from electromagnetic radiation reflected from the web 100. Conventionally, infrared measuring apparatuses may use signal interrupting to reduce measurement low frequency noise. Low frequency noise (ranging from DC to approximately 100 hertz) occurs due to slow drifting of detector properties and external, uncontrolled sources of incident infrared radiation. Typically, in conventional infrared measuring apparatuses, signal interrupting consists of rapid periodic interruption of the infrared source, usually by means of a spinning aperture wheel or a resonant oscillator driving a tuning fork type of shutter.

Low frequency noise, often called "1/f noise," is reduced in these conventional devices by means of tuned sequential electronics stages (filters) that eliminate the low frequency components. For example, filtering using capacitive coupling, in which a signal is passed through a serial capacitor, may effectively block the DC and low frequency components. Use of interruption signal processing is undesirable since a detector element is not measuring the object to be tested while the source is blocked. In a periodically interrupting device, such as one interrupted by a tuning fork, the blocked signal may be 50% or more of the available signal. Additionally, periodic interrupting may introduce aliasing error which is a generation of false signal patterns as the interrupting frequency interferes with the sensor sampling frequency, noise or some pseudo-random pattern of the measured sampling.

The measuring apparatus 10 of the present invention uses a low, variable rate of interrupting the light source 22 with the chopper mechanism 50. The detector elements 90a-90f take measurements when the light source 22 is fully blocked to serve as a zero determination or "dark condition" value. The dark condition value signals have as three major components electronic offsets inherent in each detector element 90a-90f, any detector element signal produced by ambient infrared light, and changes in detector dark current. Under static conditions, any ambient component may tend to remain constant and the detector element related component should change very slowly as a function of temperature and long term detector element drift. On a scanning system, the background may be varying and may result in a significantly varying background infrared source, thus requiring more frequent measuring of "dark condition" values. The system processor 60 uses the dark condition values to correct on-line measurement signals generated by the detector elements 90a-90f when the light source 22 is not blocked.

The chopper rate can be controlled to vary over a range of rates from 0.1 to about 30 chops per second with reciprocating chopping, as opposed to continuous rotary action. Preferably, the fraction of chopped time is no greater than about 1% of real time. The chopper stepper motor 54 operates asynchronously to move the chopper 52 into a position fully blocking the light source 22 and allows angular accuracy with separately controlled acceleration and maximum speed so that actual interruption dwell time can be kept constant as the chop rate varies. This relatively slow chopper rate means that no high-pass filter needs to be inserted in subsequent processing to eliminate the low frequency component. Additionally, this relatively slow chopper rate is in contrast to the 50 to 1000 interruptions per second used by conventional lead salt detectors. Nominally, the chopper 52 interrupts the light source 22 for durations of approximately 8-16 milliseconds at a rate of one interruption per second. The nominal chopper rate of once per second is generally adequate for maintaining electronic stability. However, this chopper rate may be inadequate for compensating for variations in background radiation. For example, a chopper rate of once per second and corresponding measuring of the dark condition value may be inadequate if there is a rapidly varying source of background infrared light (such as might be encountered in a factory situation with moving high temperature emitters in the field of view).

To provide adequate but not too frequent chopping, a chop rate is initially set at a rate of one chop per second. Generally, the required chopper rate is determined by comparing current dark conditions or corresponding baseline noise values with previous dark condition or corresponding baseline noise values. If necessary, this chop rate may be varied by a technician by changing a constant in an electronic file stored, for example, in a scanner device in which the apparatus 100 is provided.

Advantageously, there is no required periodicity or regularity to the chopper interruption rate of the chopper mechanism 50. The chopper controller 56 is individually commanded for each interrupt by a sensor control portion of the processor 60, is controllable for rate and is controlled asynchronously. The chopper rate can be changed. This controllability allows the measuring apparatus 10 of the present application to maximize the fraction of time that it is measuring substantially accurately over a wide range of conditions. Preferably, the chopper control is independent of the detector sampling control with the sampling occurring substantially continuously and interrupting occurring as needed.

The chopper motor 54 provides the ability to adjust the chopper rate from 0.1 to approximately thirty hertz with high time resolution. The chopper motor 54 should be responsive enough to allow reciprocating blocking as opposed to continuous rotary blocking at a rate of thirty interrupts per second. Thus, the chopper 52 blocks the light source 22 for practically as long or as short a time as required.

Additionally, as mentioned above, the measuring apparatus 10 of the present invention preferably includes a "synch" detector 92 to detect the precise timing of the chopper mechanism 50 so as to permit accurate measurement determination. The system processor 60 receives this silicon "synch" detector signal, which, in a working embodiment, comprises a square wave pulse, for use in signal processing and as needed.

An actual interrupt consists of a command from the system processor 60 to the controller 56 to start the chopper motor 54. The controller 56 may be preprogrammed with a predefined acceleration, deceleration and various chop rates, one of which is defined by a technician as noted above. The chopper motor 54 accelerates the chopper 52 through some angle and it then enters the first slot 28a defined in the illumination unit support 28, see FIG. 3. For example, in a working embodiment, the chopper 52 has a first transition time of 3.1 ms, a period of 10.4 ms during which the light source 22 is completely blocked, and a second transition time of 3.1 ms for a total chop time of 16.6 ms. If samples from the detector elements 90a-90f are collected at 5000 samples/second, then 10.4 ms of total dark time means there are approximately 52 samples collected when the chopper 52 completely occludes the light source 22. Since the InGaAs detector elements of the illustrated embodiment have a fast response time, these measurements are considered valid although it is acceptable to discard from each entering and leaving edge, i.e., corresponding to the first and second transition times, an additional three measurements. Thus approximately 46 dark condition samples may be used to normalize measurement data. Using the above numbers, the time that the measuring apparatus 10 is not measuring properties/characteristics of the paper web 100 is less than two percent of the operating time of the measuring apparatus 10.

In the illustrated embodiment, the system processor 60 uses the square wave synch detector pulse 92 to determine which samples collected when the chopper 52 occludes the light source 22 are deleted. For example, a predefined number of samples outside each of the entering and trailing edges of the square wave pulse may be deleted, as well as a predefined number of samples inside each of the entering and trailing edges of the square wave pulse. Hence, the first transition time corresponds to the predefined samples inside and outside the entering edge that are deleted and the second transition time corresponds to the predefined samples inside and outside the trailing edge that are deleted.

The light source 22 further comprises a light source intensity controller 27, see FIG. 3, for finely controlling the voltage provided to the lamp 26 to a reference level appropriate for the specific lamp used. The voltage intensity is preferably pulse width modulated with a crystal controlled counter so that each possible level is very stable. The light source 22 power is preferably supplied as a ten kilohertz square wave AC, so that the transition time between full high and full low is negligibly short. The range of power provided for controlling the intensity of the light source 22 is preferably from zero volts to the maximum voltage level for the specific light source used, and is controlled by the light source intensity controller 27 using a latched digital command, for example, 00000=0% and 11111=100% so that the light source intensity is divided into $2^5$ or 32 parts with each part or step being 3.125%. Of course the digital command could be more or less than 5 bits as required.

Lamp life decreases precipitously if the lamp operates at high power, i.e., near its 100% power rating. Preferably, the light source 22 operates, nominally, at 75% of its power rating, as controlled by the digital control signal from the light source intensity controller 27 discussed above.

As noted above, the signals from the detector elements 90a-90f travel through current-to-voltage pre-amplifiers, each of which corresponds to one of the detector elements 90a-90f. The current-to-voltage pre-amplifiers are mounted to the detector board 94. Output signals from the pre-amplifiers are provided to a gain board (not shown). The gain board comprises a plurality of digitally controlled offset nulling circuits (not shown), one of which corresponds to each detector element 90a-90f. Each offset nulling circuit sums the voltage signal from its corresponding pre-amplifier with an offset nulling voltage controlled by a setting given by the system processor 60 so as to null or cancel signals resulting from background radiation, detector element dark current leakage and amplifier offsets. The offset nulling signal is determined during a standardization operation and comprises the summation of background radiation when light from the source 22 is blocked so as not to be reflected from the web and reach the corresponding detector element, dark current from the corresponding detector element and amplifier offsets (due to intrinsic voltage offsets in the corresponding preamplifier and a corresponding digitally controlled variable gain amplifier, to be described below).

The offset nulling signal is generated by digital to analog conversion controlled by the system processor. During a portion of the standardize operation, detector signals are measured (without illumination) at the highest gain step. The system processor steps the digital to analog converter for each measurement channel such that the signal received by the system processor for each measurement channel is approximately zero volts. This portion of the standardize operation nulls any offset signals that may be due to amplifier offsets or detector dark current. The offset nulling signal is held constant during material property measurement operation of the apparatus 10 until changed during a subsequent standardization operation.

The gain board further comprises, for each detector element 90a-90f, a digitally controlled variable gain channel amplifier (not shown). The offset nulling signals, produced by the process described above, are summed with each detector signal at the input of the digital controlled variable gain amplifier for that detector. Each digitally controlled gain amplifier provides a gain of between 0-90 dB, such that its signal has sufficient resolution to be received by a digitizer, i.e., an analog-to-digital converter, (not shown) forming part of the system processor 60. In the illustrated embodiment, only a single digitizer is provided in the system processor 60. In response to a digital gain value generated by the system processor 60, each variable gain channel amplifier is capable of effecting amplification in 16 steps of six dB increments between 0-90 dB, wherein each step results in a doubling of gain from the prior step.

The system processor 60 periodically determines if each output from the digitizer and corresponding to one of the detector elements 90a-90f is at an acceptable value, i.e., near the center range of the digitizer. If not, the system processor 60 will change the corresponding digital gain value so as to change the gain step for the detector element's corresponding variable gain channel amplifier so that the digitizer is outputting a signal near or within its center range.

The actual gain provided by a digitally controlled variable gain channel amplifier may differ from a nominal value because of component tolerances and electronic drift. Hence, each variable gain channel amplifier may be tested at each of the sixteen gain steps during a portion of the standardization operation with the results stored in a table of actual gain step values in the system processor 60. The calibration operation involves, for each gain channel amplifier, the system processor 60 controlling a calibration circuit causing it to provide a first calibration voltage signal to the gain board, i.e., bypassing the corresponding detector element and the corresponding pre-amplifier on the detector board, and with the gain channel amplifier programmed to provide amplification at the first amplification step, and measuring the output from the gain channel amplifier using the digitizer. The output is then stored in memory by the system processor 60. The first calibration voltage is again input into the gain board, with the gain channel amplifier being programmed to provide amplification at the second amplification step. The output is measured by the digitizer, compared to the digitizer value stored in memory for the first amplification step/first calibration voltage such that the compared value, i.e., the calibration ratio of the value for the second amplification step/first calibration voltage to the value for the first amplification step/first calibration voltage is stored as a corrected first amplification or gain step in the table of actual gain step values in the system processor 60.

Next, a second calibration voltage, which is approximately one-half of the first calibration voltage, is provided to the gain board with the gain channel amplifier programmed to provide amplification at the second amplification step. The output from the digitizer is measured and then stored in memory by the system processor 60. The second calibration voltage is again input into the gain board, with the gain channel amplifier programmed to provide amplification at the third amplification step. The output is measured by the digitizer, compared to the digitizer value stored in memory for the second amplification step/second calibration voltage such that the compared value, i.e., the calibration ratio of the value for the third amplification step/second calibration voltage to the value for the second amplification step/second calibration voltage is stored as a corrected second amplification or gain step in the table of actual gain step values in the system processor 60. This calibration process continues until empirically derived gain steps have been determined for each of the remaining amplification or gain steps (3 through 16). These stored actual gain step values are used to calculate relative signal levels between the detector elements 90a-90f for the purpose of comparing signal levels of the detector elements 90a-90f.

The independent gain capability for each digitally controlled variable gain amplifier allows the digitizer to operate within its optimum (most linear and best resolution) range. For example, a low mass product absorbs little, if any, of the measurement wavelengths, so that the resulting signals from the separate detector elements 90a-90f will all be similar in magnitude. Therefore for a low mass product, the electronic gain, i.e., amplification step for each digitally controlled variable gain amplifier is set by the system processor 60 to substantially the same value, specifically a value that places the output signal from each amplifier near the center of the input range for the digitizer in the system processor 60. For a product that absorbs a significant portion of electromagnetic radiation falling within a band corresponding to one of the detector elements 90a-90f, the one detector element will produce a much smaller signal than other detector elements sensing electromagnetic radiation, which is only slightly absorbed and falling within other bands. In this high mass product, a different gain, i.e., a different amplification step, will be selected for the digitally controlled variable gain amplifier corresponding to the one detector element so as to result in similar signal output levels from all variable gain amplifiers, once again near the center range of the digitizer in the system processor 60. By knowing the actual values of the amplification or gain steps (stored in the actual gain step value table) assigned to each digitally controlled variable gain amplifier, the system processor 60 is able to determine ratios of absorption between two or more different detector elements 90a-90f. The relative gain between detector elements 90a-90f is needed for making ratio measurements between the detector elements 90a-90f. This method of independent variable gain amplifier gain greatly extends the "dynamic range" of the measuring apparatus 10 of the present application.

Each of the detector element outputs is preferably sampled or measured continuously at the nominal rate of 5000 times per second such that each detector element's corresponding digitally controlled variable gain amplifier provides a like number of amplified signals to the digitizer in the system processor 60. Due to the InGaAs detector elements 90a-90f relatively fast response rates, increased measurement rates in a range of 20,000 samples per second to 1,000,000 samples per second are possible, with similarly fast response electronic systems. The calculated value of each "wavelength" detector element 90a-90f is its measured output divided by the gain of its associated digitally controlled variable gain amplifier. The gain is determined by multiplying the gain steps together. For a gain step of four, the gain comprises: gain step 1×gain step 2×gain step 3×gain step 4.

The "synch" detector element, the silicon "synch" detector 92 in the illustrated embodiment, does not require a digitally controlled variable gain amplifier, but does require a non-adjustable gain amplifier (not shown). The "synch" detector element channel varies between less than 100 milli-volts, indicating the source is interrupted or blocked, and greater than four volts, indicting the source is open or on.

A single measurement of each detector element 90a-90f comprises a data set. The digitizer in combination with a conventional multiplexer samples each detector element at a nominal rate of 5000 samples per second, such that the digitizer is sampling at a rate of 30,000/second.

The measuring apparatus 10 may perform a "standardization" operation every 30-120 minutes so as to periodically normalize for detector element drift, electronic drift or light source drift. During this operation, material properties/characteristics measurements are not performed.

A portion of the standardization operation involves moving the chopper 52 to a position to fully block light energy directed toward the fiber optic ferrule 34, see FIG. 3. This stops light from entering the path defined by the first optical fibers 112 such that no energy exits the cylindrical member 32g. The standardize shutter 72 is moved allowing energy to enter the standardize ferrule 36. Energy from the light source 22 passes through the third optical fibers 142, which are randomly positioned within the housing 32, and irradiates each detector element 90a-90f. The system processor 60 then reads a light signal generated by each detector element 90a-90f, without influence of reflected light from the web 100, and stores these values as "DarkOpen1$_x$" values.

After the "DarkOpen1x" signal values are measured, but while the chopper 52 still blocks energy from entering the fiber optic ferrule 34, the shutter 72 is moved to a position, as illustrated in FIG. 3, so as to block all light entering the bore 28c; hence, no energy enters the standardize ferrule 36. This blocking position is the "normal" position of the shutter 72 during on-line measurement. With all energy from the light source 22 blocked from the detector elements 90a-90f, the system processor 60 reads the detector element signals and stores these values as "DarkClosed$_x$" values.

After the dark signal values are measured, but while the chopper 52 still blocks energy from entering the fiber optic ferrule 34, the shutter 72 is moved allowing energy to again enter the standardize ferrule 36. The system processor 60 then reads a light signal generated by each detector element 90a-90f, without influence of reflected light from the web 100, and stores these values as "DarkOpen2$_x$" values.

The system processor 60 determines standardize values and standardize ratios based on these measurements from each of the detectors 90a-90f using the following equations:

Standardize Values

Stdz $R$ Value=[(DarkOpen1$_R$+DarkOpen2$_R$)/2]−DarkClosed$_R$

Stdz $M$1 Value=[(DarkOpen1$_{M1}$+DarkOpen2$_{M1}$)/2]−DarkClosed$_{M1}$

Stdz $M$2 Value=[(DarkOpen1$_{M2}$+DarkOpen2$_{M2}$)/2]−DarkClosed$_{M2}$

Stdz $M$3 Value=[(DarkOpen1$_{M3}$+DarkOpen2$_{M3}$)/2]−DarkClosed$_{M3}$

Stdz $M$4 Value=[(DarkOpen1$_{M4}$+DarkOpen2$_{M4}$)/2]−DarkClosed$_{M4}$

Stdz $M$5 Value=[(DarkOpen1$_{M5}$+DarkOpen2$_{M5}$)/2]−DarkClosed$_{M5}$ where

DarkOpen1$_R$ is the "DarkOpen1$_x$" value measured during the standardize operation by a reference detector element; in the illustrated embodiment, the reference detector element comprises detector element 90a (the reference detector element could be defined as any one of the detector elements 90a-90f);

DarkOpen2$_R$ is the "DarkOpen2$_x$" value measured during the standardize operation by the reference detector element 90a;

DarkClosed$_R$ is the "DarkClosed$_x$" value measured during the standardize operation by the reference detector element 90a;

DarkOpen1$_{M1}$ is the "DarkOpen1$_x$" value measured during the standardize operation by detector element 90b;

DarkOpen2$_{M1}$ is the "DarkOpen2$_x$" value measured during the standardize operation by the detector element 90b;

DarkClosed$_{M1}$ is the "DarkClosed$_x$" value measured during the standardize operation by the detector element 90b;

DarkOpen1$_{M2}$ is the "DarkOpen1$_x$" value measured during the standardize operation by detector element 90c;

DarkOpen2$_{M2}$ is the "DarkOpen2$_x$" value measured during the standardize operation by the detector element 90c;

DarkClosed$_{M2}$ is the "DarkClosed$_x$" value measured during the standardize operation by the detector element 90c;

DarkOpen1$_{M3}$ is the "DarkOpen1$_x$" value measured during the standardize operation by detector element 90d;

DarkOpen2$_{M3}$ is the "DarkOpen2$_x$" value measured during the standardize operation by the detector element 90d;

DarkClosed$_{M3}$ is the "DarkClosed$_x$" value measured during the standardize operation by the detector element 90d;

DarkOpen1$_{M4}$ is the "DarkOpen1$_x$" value measured during the standardize operation by detector element 90e;

DarkOpen2$_{M4}$ is the "DarkOpen2$_x$" value measured during the standardize operation by the detector element 90e;

DarkClosed$_{M4}$ is the "DarkClosed$_x$" value measured during the standardize operation by the detector element 90e;

DarkOpen1$_{M5}$ is the "DarkOpen1$_x$" value measured during the standardize operation by detector element 90f; and DarkOpen2$_{M5}$ is the "DarkOpen2$_x$" value measured during the standardize operation by the detector element 90f;

DarkClosed$_{M5}$ is the "DarkClosed$_x$" value measured during the standardize operation by the detector element 90f.

Standardize Ratios

Stdz $M$1 Ratio=(Stdz $M$1 Value/Stdz $R$ Value)*Int$M$1Stnd

Stdz $M$2 Ratio=(Stdz $M$2 Value/Stdz $R$ Value)*Int$M$2Stnd

Stdz $M$3 Ratio=(Stdz $M$3 Value/Stdz $R$ Value)*Int$M$3Stnd

Stdz $M$4 Ratio=(Stdz $M$4 Value/Stdz $R$ Value)*Int$M$4Stnd

Stdz $M$5 Ratio=(Stdz $M$5 Value/Stdz $R$ Value)_*Int$M$5Stnd

Where: IntMxStnd=Internal Standard Mx Ratio Constant; calculated as discussed below.

During on-line operation of the measuring apparatus 10, the system processor 60 corrects the on-line measurement signals generated by the detectors 90a-90f via the following equations:

Raw Measurement Ratios

The following are the raw ratio values:

$$\text{Raw } M1 \text{ Ratio} = \frac{(R - R_o)/\text{Total Gain for } R}{(M1 - M1_o)/\text{Total Gain for } M1}$$

-continued $$\text{Raw } M2 \text{ Ratio} = \frac{(R - R_o)/\text{Total Gain for } R}{(M2 - M2_o)/\text{Total Gain for } M2}$$

$$\text{Raw } M3 \text{ Ratio} = \frac{(R - R_o)/\text{Total Gain for } R}{(M3 - M3_o)/\text{Total Gain for } M3}$$

$$\text{Raw } M4 \text{ Ratio} = \frac{(R - R_o)/\text{Total Gain for } R}{(M4 - M4_o)/\text{Total Gain for } M4}$$

$$\text{Raw } M5 \text{ Ratio} = \frac{(R - R_o)/\text{Total Gain for } R}{(M5 - M5_o)/\text{Total Gain for } M5}$$

wherein:

M1 is the on-line signal generated by detector element 90b when the chopper 52 is not inserted in the slot 28a and the standardize shutter 72 is inserted in the slot 28d;

M1o is a chopper blocking signal generated by detector element 90b when the chopper 52 and the shutter 72 are inserted in the slots 28a and 28d during on-line operation of the measuring apparatus 10 outside of a standardize operation;

Total Gain for M1 is determined by taking the actual gain step value stored in the gain step table in the system processor 60 for the corresponding variable gain channel amplifier and multiplying that gain step by any lower gain steps, e.g., for a gain step of 4, the total gain=gain step 1×gain step 2×gain step 3×gain step 4.

M2 is the on-line signal generated by detector element 90c when the chopper 52 is not inserted in the slot 28a and the standardize shutter 72 is inserted in the slot 28d;

M2o is a chopper blocking signal generated by detector element 90c when the chopper 52 and the shutter 72 are inserted in the slots 28a and 28d during on-line operation of the measuring apparatus 10 outside of a standardize operation;

Total Gain for M2 is determined by taking the actual gain step value stored in the gain step table in the system processor 60 for the corresponding variable gain channel amplifier and multiplying that gain step by any lower gain steps;

M3 is the on-line signal generated by detector element 90d when the chopper 52 is not inserted in the slot 28a and the standardize shutter 72 is inserted in the slot 28d;

M3o is a chopper blocking signal generated by detector element 90d when the chopper 52 and the shutter 72 are inserted in the slots 28a and 28d during on-line operation of the measuring apparatus 10 outside of a standardize operation;

Total Gain for M3 is determined by taking the actual gain step value stored in the gain step table in the system processor 60 for the corresponding variable gain channel amplifier and multiplying that gain step by any lower gain steps;

M4 is the on-line signal generated by detector element 90e when the chopper 52 is not inserted in the slot 28a and the standardize shutter 72 is inserted in the slot 28d;

M4o is a chopper blocking signal generated by detector element 90e when the chopper 52 and the shutter 72 are inserted in the slots 28a and 28d during on-line operation of the measuring apparatus 10 outside of a standardize operation;

Total Gain for M4 is determined by taking the actual gain step value stored in the gain step table in the system processor 60 for the corresponding variable gain channel amplifier and multiplying that gain step by any lower gain steps;

M5 is the on-line signal generated by detector element 90f when the chopper 52 is not inserted in the slot 28a and the standardize shutter 72 is inserted in the slot 28d;

M5o is a chopper blocking signal generated by detector element 90f when the chopper 52 and the shutter 72 are inserted in the slots 28a and 28d during on-line operation of the measuring apparatus 10 outside of a standardize operation;

Total Gain for M5 is determined by taking the actual gain step value stored in the gain step table in the system processor 60 for the corresponding variable gain channel amplifiers and multiplying that gain step by any lower gain steps;

R is the on-line signal generated by detector element 90a when the chopper 52 is not inserted in the slot 28a and shutter 72 is inserted in the slot 28d;

Ro is a chopper blocking signal generated by the detector element 90a when the chopper and the shutter 72 are inserted in the slots 28a and 28d during on-line operation of the measuring apparatus 10 outside of a standardize operation; and Total Gain for R is determined by taking the actual gain step value stored in the gain step table in the system processor 60 for the corresponding variable gain channel amplifier and multiplying that gain step by any lower gain steps.

Standardized Corrected Measurement Ratios

The following are the standardize corrected ratios.

StdzCorr M1 Ratio=Raw M1 Ratio*Stdz M1 Ratio

StdzCorr M2 Ratio=Raw M2 Ratio*Stdz M2 Ratio

StdzCorr M3 Ratio=Raw M3 Ratio*Stdz M3 Ratio

StdzCorr M4 Ratio=Raw M4 Ratio*Stdz M4 Ratio

StdzCorr M5 Ratio=Raw M5 Ratio*Stdz M5 Ratio

Derivation of Internal Standard Mx Ratio Constants:

The following calculations are performed only when the sensor is initially calibrated during manufacturing.

A sample or "golden standard" is measured when the sensor is initially calibrated during manufacture and the golden standard remains with the manufacturing department. The golden standard is measured initially to determine: Stdz M1 Ratio, Stdz M2 Ratio, Stdz M3 Ratio, Stdz M4 Ratio and Stdz M5 Ratio with each of corresponding IntM1Stnd, IntM2Stnd, IntM3Stnd, IntM4Stnd, and IntM5Stnd being set=1. Those values are then used in combination with collected Raw M1 Ratio, Raw M2 Ratio, Raw M3 Ratio, Raw M4 Ratio, and Raw M5 Ratio, also determined on the golden standard during manufacture, to calculate StdzCorr M1 Ratio, StdzCorr M2 Ratio, StdzCorr M3 Ratio, StdzCorr M4 Ratio, and StdzCorr M5 Ratio values. Thereafter, during manufacture, the calculated StdzCorr X Ratio values based on the golden standard are defined respectively as $\text{StdzCorr M1 Ratio}_{Golden\ Standard}$, $\text{StdzCorr M2 Ratio}_{Golden\ Standard}$, $\text{StdzCorr M3 Ratio}_{Golden\ Standard}$, $\text{StdzCorr M4 Ratio}_{Golden\ Standard}$, $\text{StdzCorr M5 Ratio}_{Golden\ Standard}$.

If some main portion of the sensor optics are repaired after manufacture, then the process described above may be duplicated in the field using a secondary sample whose reflectance characteristics are traceable to the golden standard sample. From those values, IntM1Stnd, IntM2Stnd, IntM3Stnd, IntM4Stnd, IntM5Stnd are determined using the following equations:

$$IntM1Stnd = \frac{1}{StdzCorr\ M1\ Ratio_{GoldenStandard}}.$$

$$IntM2Stnd = \frac{1}{StdzCorr\ M2\ Ratio_{GoldenStandard}}.$$

$$IntM3Stnd = \frac{1}{StdzCorr\ M3\ Ratio_{GoldenStandard}}.$$

$$IntM4Stnd = \frac{1}{StdzCorr\ M4\ Ratio_{GoldenStandard}}.$$

$$IntM5Stnd = \frac{1}{StdzCorr\ M5\ Ratio_{GoldenStandard}}.$$

It is noted that the "dark condition" values, which are used to correct on-line measurement signals generated by the detector elements 90a-90f, are taken into consideration during the calculations of Raw M1 Ratio, Raw M2 Ratio, Raw M3 Ratio, Raw M4 Ratio and Raw M5 Ratio via M1o, M2o, M3o, M4o, M5o, and Ro.

Each of StdzCorr M1 Ratio, StdzCorr M2 Ratio, StdzCorr M3 Ratio, StdzCorr M4 Ratio, and StdzCorr M5 Ratio comprises a ratio of the infrared light at two wavelengths reflected from the web 100, noted above, which ratio correlates to the area weight of a property/characteristic on or in the web 100 to be measured. StdzCorr M1 Ratio, StdzCorr M2 Ratio, StdzCorr M3 Ratio, StdzCorr M4 Ratio, and StdzCorr M5 Ratio are used by the system processor 60 as inputs into a principal component analysis algorithm, which algorithm would be apparent to one skilled in the art, to determine various material properties/characteristics of the web 100 such as fiber content, moisture content, and coating material content such as latex, clay, calcium carbonate and plastic.

In FIG. 5, first and second infrared measuring apparatuses 202 and 204 are positioned on opposite sides of a moving web 100 so as, for example, to measure coatings provided on both sides of the web 100 or surface moisture on both sides of the web 100. The first, second and third fiber optic structures 110, 80 and 140 comprising part of each apparatus 202 and 204 are not illustrated in FIG. 5. The first and second apparatuses 202 and 204 are constructed in essentially the same manner as apparatus 10 illustrated in FIGS. 1-4 and are positioned such that the spot S of light generated by apparatus 202 does not generate noise or interference for apparatus 204 and vice versa.

What is claimed is:

1. A measuring apparatus comprising:
an illumination unit including a source of electromagnetic radiation;
fiber optic apparatus including first fiber optic structure comprising a bundle of first optical fibers having first input ends for receiving at least a portion of electromagnetic radiation emitted from said radiation source and first output ends for directing the received radiation to a web of material, and second fiber optic structure comprises a bundle of second optical fibers having second input ends for receiving radiation reflected from said web of material and second output ends for directing said reflected radiation to a sensing apparatus, said first output ends being randomly intermixed with said second input ends and being positioned at an angle of from about 30 degrees to about 60 degrees to said web of material such that said second input ends receive substantially only diffuse electromagnetic radiation reflected from said web of material; and
wherein said sensing apparatus comprises a first detector for sensing electromagnetic radiation of a first wavelength band and generating a corresponding first output signal and a second detector for sensing electromagnetic radiation of a second wavelength band and generating a corresponding second output signal indicative of a first property to be measured of said web of material.

2. A measuring apparatus as set forth in claim 1, wherein said electromagnetic radiation of a first wavelength band comprises electromagnetic radiation of a first infrared wavelength band and said electromagnetic radiation of a second wavelength band comprises electromagnetic radiation of a second infrared wavelength band, and said first output signal comprises a reference signal and said second output signal is compared to said first output signal via a processor to determine said first property of said web of material.

3. A measuring apparatus as set forth in claim 2, wherein said sensing apparatus further comprises:
a third detector for sensing electromagnetic radiation of a third infrared wavelength band and generating a corresponding third output signal indicative of a second property to be measured of said web of material, said third output signal is compared to said first output signal via a processor to determine said second property of said web of material;
a fourth detector for sensing electromagnetic radiation of a fourth infrared wavelength band and generating a corresponding fourth output signal indicative of a third property to be measured of said web of material, said fourth output signal is compared to said first output signal via a processor to determine said third property of said web of material;
a fifth detector for sensing electromagnetic radiation of a fifth infrared wavelength band and generating a corresponding fifth output signal indicative of a fourth property to be measured of said web of material, said fifth output signal is compared to said first output signal via a processor to determine said fourth property of said web of material; and
a sixth detector for sensing electromagnetic radiation of a sixth infrared wavelength band and generating a corresponding sixth output signal indicative of a fifth property to be measured of said web of material, said sixth output signal is compared to said first output signal via a processor to determine said fifth property of said web of material.

4. A measuring apparatus as set forth in claim 1, wherein said first optical fibers are randomly routed such that said first input and output ends are randomly positioned and said second optical fibers are randomly routed such that said second input and output ends are randomly positioned.

5. A measuring apparatus as set forth in claim 1, wherein all of said second optical fibers are of substantially the same length.

6. A measuring apparatus as set forth in claim 1, wherein said illumination unit further comprises a support to which said electromagnetic radiation source is coupled.

7. A measuring apparatus as set forth in claim 6, further comprising a chopper mechanism including a chopper element, said illumination unit support comprising a first slot through which said chopper element is permitted to enter so as to prevent light generated by said electromagnetic radiation source from passing through a main illumination opening in said illumination unit support to said input end of said first fiber optic structure.

8. A measuring apparatus comprising:
an illumination unit including a source of electromagnetic radiation, said illumination unit comprising a support to which said electromagnetic radiation source is coupled;
fiber optic apparatus including first fiber optic structure comprising a bundle of first optical fibers having first input ends for receiving at least a portion of electromagnetic radiation emitted from said radiation source and first output ends for directing the received radiation to a web of material, and second fiber optic structure comprising a bundle of second optical fibers having second input ends for receiving radiation reflected from said web of material and second output ends for directing said reflected radiation to a sensing apparatus, said first output ends being randomly intermixed with said second input ends and being;
a chopper mechanism including a chopper element, said illumination unit support comprising a first slot through which said chopper element is permitted to enter so as to prevent light generated by said electromagnetic radiation source from passing through a main illumination opening in said illumination unit support to said input end of said first fiber optic structure; and
a standardize mechanism including a shutter, said illumination unit support comprising a second slot through which said shutter is permitted to pass so as to prevent electromagnetic radiation generated by said electromagnetic radiation source from passing through an opening to an input end of a third fiber optic structure;
wherein said sensing apparatus comprises a first detector for sensing electromagnetic radiation of a first wavelength band and generating a corresponding first output signal and a second detector for sensing electromagnetic radiation of a second wavelength band and generating a corresponding second output signal indicative of a first property to be measured of said web of material.

9. A measuring apparatus as set forth in claim 8, wherein said third fiber optic structure comprises a bundle of third optical fibers having third input ends for receiving at least a portion of the electromagnetic radiation emitted from said electromagnetic radiation source when said shutter is absent from said second slot and third output ends for directing said light to said sensing apparatus.

10. A measuring apparatus as set forth in claim 8, wherein said fiber optic apparatus further comprises an optical fiber housing in which at least portions of said first and second fiber optic structures are housed.

11. A measuring apparatus system comprising:
an illumination unit comprising an electromagnetic radiation source;
electromagnetic radiation guide apparatus including a first radiation guide structure comprising a bundle of first optical fibers having first input ends for receiving at least a portion of radiation emitted from said electromagnetic radiation source and first output ends for directing the received radiation onto a web of material, and a second radiation guide structure comprising a bundle of second optical fibers having second input ends for receiving radiation reflected from said web of material and second output ends for directing said reflected radiation to a sensing apparatus, said first output ends being randomly intermixed with said second input ends and are positioned at an angle of from about 30 degrees to about 60 degrees to said web of material such that said second input ends receive substantially only diffuse radiation reflected from said web of material;
wherein said sensing apparatus comprises a first detector for sensing electromagnetic radiation of a first wavelength band and generating a corresponding first output signal and a second detector for sensing electromagnetic radiation of a second wavelength band and generating a corresponding second output signal; and
a processor for receiving said first and second output signals and determining a property of said web of material using said first and second output signals.

12. A measuring apparatus system as set forth in claim 11, wherein said sensing apparatus further comprises:
a third detector for sensing electromagnetic radiation of a third wavelength band and generating a corresponding third output signal;
a fourth detector for sensing electromagnetic radiation of a fourth wavelength band and generating a corresponding fourth output signal;
a fifth detector for sensing electromagnetic radiation of a fifth wavelength band and generating a corresponding fifth output signal; and
a sixth detector for sensing electromagnetic radiation of a sixth wavelength band and generating a corresponding sixth output signal.

13. A measuring apparatus system as set forth in claim 12, wherein said first output signal comprises a reference signal and respective magnitudes of said second, third, fourth, fifth and sixth output signals and a magnitude of said first output signal are used by said processor to determine first, second, third, fourth and fifth properties of said web of material.

14. A measuring apparatus system as set forth in claim 11, wherein said first optical fibers are randomly routed such that said first input ends and said first output ends are randomly positioned and said second optical fibers are randomly routed such that said second input ends and said second output ends are randomly positioned.

15. A measuring apparatus system comprising:
an illumination unit comprising an electromagnetic radiation source;
electromagnetic radiation guide apparatus including a first radiation guide structure having an input end for receiving at least a portion of radiation emitted from said electromagnetic radiation source and an output end for directing the received radiation onto a web of material, and a second radiation guide structure having an input end for receiving radiation reflected from said web of material and an output end for directing said reflected radiation to a sensing apparatus;
a chopper mechanism including a chopper movable within a slot provided in an illumination unit support so as to prevent electromagnetic radiation generated by said electromagnetic radiation source from passing through a main illumination opening in said illumination unit support to said input end of said first radiation guide structure;
a standardize mechanism including a shutter, said illumination unit support comprising a second slot through which said shutter is permitted to pass so as to prevent electromagnetic radiation generated by said radiation source from passing through an opening to an input end of a third radiation guide structure;
wherein said sensing apparatus comprises a first detector for sensing electromagnetic radiation of a first wavelength band and generating a corresponding first output signal and a second detector for sensing electromagnetic radiation of a second wavelength band and generating a corresponding second output signal; and a processor for receiving said first and second output signals and determining a property of said web of material using said first and second output signals.

16. A measuring apparatus system as set forth in claim 15, wherein said third radiation guide structure comprises a bundle of third optical fibers having third input ends for receiving at least a portion of the electromagnetic radiation emitted from said electromagnetic radiation source when said shutter is absent from said second slot and third output ends for directing said reflected radiation to said sensing apparatus.

17. An optical system for directing electromagnetic radiation toward a web of material and for receiving radiation backscattered from said web, said system comprising:

a bundle of first optical fibers having first input ends for receiving electromagnetic radiation and directing said electromagnetic radiation to said web of material from first output ends; and a bundle of second optical fibers having second input ends for receiving electromagnetic radiation backscattered from said web of material and second output ends for passing backscattered radiation received from said web to at least one electromagnetic radiation output port, wherein said first output ends are randomly intermixed with said second input ends;

wherein said first output ends and said second input ends are positioned at an angle of from about 30 degrees to about 60 degrees to said web of material such that said second input ends receive substantially only diffuse radiation reflected from said web.

18. An optical system as set forth in claim 17, wherein said first optical fibers are randomly routed such that said first input ends and said first output ends are randomly positioned and said second optical fibers are randomly routed such that said second input ends and said second output ends are randomly positioned.

19. An optical system as set forth in claim 18, wherein all of said second optical fibers are of substantially the same length.

20. An optical system as set forth in claim 17, further comprising a bundle of third optical fibers having third input ends for receiving radiation and directing said radiation to said at least one port from third output ends.

* * * * *